United States Patent
Tamaoki et al.

(10) Patent No.: US 10,544,453 B2
(45) Date of Patent: Jan. 28, 2020

(54) METHOD FOR DETECTING NUCLEIC ACID AMPLIFICATION PRODUCT IN REAL TIME

(71) Applicant: PHC HOLDINGS CORPORATION, Tokyo (JP)

(72) Inventors: Yuichi Tamaoki, Gunma (JP); Akifumi Iwama, Tsukuba (JP); Yasuaki Sonoda, Gunma (JP)

(73) Assignee: PHC HOLDINGS CORPORATION, Tokyo (JP)

( * ) Notice: Subject to any disclaimer, the term of this patent is extended or adjusted under 35 U.S.C. 154(b) by 712 days.

(21) Appl. No.: 14/339,092

(22) Filed: Jul. 23, 2014

(65) Prior Publication Data

US 2014/0335531 A1 Nov. 13, 2014

Related U.S. Application Data

(62) Division of application No. 12/281,540, filed as application No. PCT/JP2007/053949 on Mar. 1, 2007, now abandoned.

(30) Foreign Application Priority Data

Mar. 6, 2006 (JP) .................................. 2006-059381

(51) Int. Cl.
  *C12Q 1/686* (2018.01)
(52) U.S. Cl.
  CPC ................... *C12Q 1/686* (2013.01)
(58) Field of Classification Search
  CPC ... C12Q 1/6851; C12Q 1/686; G01N 21/6452
  See application file for complete search history.

(56) References Cited

U.S. PATENT DOCUMENTS

| 5,096,807 A | 3/1992 | Leaback |
| 2003/0148302 A1 | 8/2003 | Woo et al. |

FOREIGN PATENT DOCUMENTS

| JP | 09-504610 | 5/1997 |
| JP | 2005/512019 | 4/2005 |

(Continued)

OTHER PUBLICATIONS

International Search Report for International Application No. PCT/JP2007/053949 dated May 29, 2007.

(Continued)

*Primary Examiner* — Gautam Prakash
(74) *Attorney, Agent, or Firm* — Kratz, Quintos & Hanson, LLP

(57) ABSTRACT

There is provided an apparatus for detecting a nucleic acid amplification product in real time, which is capable of effectively excluding or reducing apparatus error factors without using a second fluorescence signal used for correction. A plurality of wells 7A are given with temperature cycles and fluorescence strength from a nucleic acid amplification product is detected in real time in each well 7A. A fluorescence measurement value [DNA]raw obtained from the well 7A and a fluorescence measurement value [DNA]bg obtained from a connection wall near the well 7A are detected, and the fluorescence measurement value [DNA]bg is subtracted from the fluorescence measurement value [DNA]raw to determine fluorescence strength [DNA]real of the well 7A.

3 Claims, 7 Drawing Sheets

(56) References Cited

FOREIGN PATENT DOCUMENTS

| JP | 2005-245310 | 9/2005 |
|---|---|---|
| WO | 95/11454 | 4/1995 |
| WO | 02/061858 A2 | 8/2002 |
| WO | 02/092118 | 11/2002 |
| WO | 02/092118 A1 | 11/2002 |
| WO | 03/067215 A2 | 8/2003 |
| WO | 2004/044221 A2 | 5/2004 |
| WO | 2004/065959 A2 | 8/2004 |

OTHER PUBLICATIONS

Thygesen, Helene H., et al., "Comparing transformation methods for DNA microarray data," BMC Bioinformatics, BioMed Central, vol. 5, No. 77 (2004), pp. 1-12.
Supplementary European Search Report dated Nov. 24, 2010.
Japanese Office Action dated Jul. 12, 2011, issued on counterpart Japanese Application No. 2006-059381 (2 pages).
English translation of Japanese Office Action dated Jul. 12, 2011, in counterpart application No. 2006-059381 (2 pages).

(8) (9)

(8) (9)

METHOD FOR DETECTING NUCLEIC ACID AMPLIFICATION PRODUCT IN REAL TIME

BACKGROUND OF THE INVENTION

Field of the Invention

This invention relates to an apparatus for real-time detecting a polynucleotide product obtained from a polymerase chain reaction (PCR).

Description of the Related Art

A PCR is a cyclic enzyme reaction to replicate a DNA chain. As the PCR is used as a template of a cycle in which PCR products (nucleic acid amplification products) replicated in previous cycles are consecutive, arrayed target molecules can be exponentially amplified. A real time PCR is to excite fluorescent material by irradiating a PCR product with excitation light using, for example, array-specific probes (TAQMAN probes) marked with two different kinds of fluorescent pigments interfering with each other, measure the strength of the fluorescence and monitor amplification of the PCR products in real time.

In quantitative use, a threshold ((6) in FIG. 7) is set in an exponential amplification region of an amplification curve for existing samples, and a point (threshold cycle number (Ct). (8) in FIG. 8) at which the threshold intersects the amplification curve is calculated. There is a linear relation between the threshold cycle number (Ct) and the initial amount of DNA of a test sample measured in terms of log value, and a calibration curve representing this linear relation can be prepared. The initial amount of DNA of the test sample is estimated based on the calibration curve. This enables correct quantitativeness based on a PCR amplification speed theory.

Here, since an actual PCR efficiency is not 100%, the concentration of an amplified PCR product is expressed by the following Equation 1.

$$[DNA]=[DNA]_0(1+e)^c \quad (1)$$

Where, [DNA]: Concentration of PCR product
  $[DNA]_0$: Initial concentration of target Template
  e: Average PCR efficiency
  c: Cycle number That is, if the average PCR efficiency (e) is 100% (i.e., e=1 in the above Equation (1)), although the concentration [DNA] of the PCR product is exponentially amplified with $2^c$, since the efficiency (e) is slowly lowered from the initial stage, through the middle stage, to the late state of the cycle, an amplification curve is as shown in FIG. 7. In FIG. 7, a horizontal axis represents the cycle number and a vertical axis represents the fluorescence strength. As shown in the figure, the fluorescence strength is exponentially amplified ((5) in FIG. 7) at the cycle initial stage, linearly amplified ((6) in FIG. 7) at the cycle middle stage, and not amplified ((7) in FIG. 7) by a plateau effect at the cycle late stage.

Chemical-reactive factors for this plateau effect are as follows.

Hydrolysis of dNTP and primer
  Deactivation of DNA polymerase (DNA synthase to make a copy of a template (cast)) by heat.
  Lowering of primer annealing efficiency by re-association of one chain PCR fragment
  Competitive material by non-specific PCR product
  Accumulation of PCR inhabitation material such as pyrophosphate
  Hydrolysis of PCR product by exonuclease activation of DNA polymerase Accordingly, the measurement in the exponential amplification region satisfying the relation of the Equation (1) is a precondition for the real time PCR (see Patent Document 1)

[Patent Document 1] Japanese Patent Application Publication No. 2005-516630
[Patent Document 2] Japanese Patent No. 2909216

As a reactive vessel used for the real time PCR, a vessel called a micro plate having a plurality (for example, 96) of wells (reactive regions constituted by concave portions) is being used in common and reactive solution having a predetermined initial DNA concentration is divisionally poured in the wells. However, an amplification curve for each of the wells of the reactive vessel becomes unbalanced due to the following apparatus error factors Error of optical system
  Concentration error of correction solution
  Divisional pour error of correction solution
  Light transmission error of cap of reactive vessel or seal film
  Contamination error of reactive vessel
  Divisional pour error of reactive vessel Here, the reactive vessel mainly uses a cheap method in which the above-mentioned seal film with an adhesive is attached to the entire region of a single side and the wells are cover by a cap. In addition, the wells are irradiated with excitation light through the seal film and fluorescence generated from the PCR product (reaction product) is detected by a light detecting part such as a CCD camera through the seal film (these components constitute an optical system). In this manner, although the seal film and the body of the reactive vessel constitute important factors of the optical system in measurement of the fluorescence strength, these components are consumable parts, it is difficult to expect optical performance with high uniformity and precision.

FIG. 4 shows an actual image of a reactive vessel before PCR, which is detected by an optical detecting part. While the circumference of wells of the reactive vessel appears to be black as a whole, the brightness of pixels of the image as a background is not necessarily constant and there occurs a spot due to contamination of the optical system or way-out light as indicated by (1) in the figure. When a PCR reaction is initiated, this spot overlaps with images (96 images appearing to be round in FIG. 5) of the wells as indicated by (2) in FIG. 5, wastefully adding to the fluorescence strength of the wells.

So, in the prior art, empty reactive vessels containing no DNA are initially prepared, and fluorescence strengths for wells are measured in such an empty state and are stored as standard correction values. Then, by performing a correcting process in which the stored correction values are subtracted from measurement values of actual fluorescence strengths, such correction of the optical system is performed. However, since errors due to contamination of the empty reactive vessels are inherent to the respective reactive vessels, if correction values by other standard empty reactive vessels are used, there occurs a problem of errors in measurement values.

In addition, in Patent Document 2, although a first fluorescence signal is corrected with a second fluorescence signal, since a solution that generates second fluorescence for reference must be added to a solution that generates first fluorescence to be originally measured, work becomes complicated and costs are raised. In addition, the solution that generates the second fluorescence can not give any effect if it can not be divisionally poured and measured with very high precision. In addition, since an especial optical filter has to be used to measure the second fluorescence and has to be exchanged for the solution that generates the first fluorescence and the solution that generates the second fluorescence every measurement, there is a problem that it takes extra time to acquire and process data.

The present invention has made to overcome the above technical problems and it is an object of the invention to provide an apparatus for detecting a nucleic acid amplification product in real time, which is capable of effectively excluding or reducing apparatus error factors without using a second fluorescence signal used for correction.

SUMMARY OF THE INVENTION

According to a first aspect of the invention, there is provided an apparatus for detecting fluorescence strength from a nucleic acid amplification product in each of a plurality of reaction regions given with temperature cycles in real time, wherein a fluorescence measurement value [DNA]raw obtained from the reaction region and a fluorescence measurement value [DNA]bg obtained from regions other than the reaction region adjacent to the reaction region are detected, and the fluorescence measurement value [DNA]bg is subtracted from the fluorescence measurement value [DNA]raw to determine fluorescence strength [DNA]real of the reaction region.

According to a second aspect of the Invention, the fluorescence measurement value [DNA]bg is a simple average value of fluorescence measurement values obtained from the regions other than the plurality of reaction regions adjacent to the reaction region, or an average value of fluorescence measurement values after the fluorescence measurement values are weighted.

According to a third aspect of the invention, the fluorescence measurement value [DNA]bg is detected every detection of the fluorescence measurement value [DNA]raw, and the fluorescence measurement value [DNA]bg is subtracted from the fluorescence measurement value [DNA]raw to determine the fluorescence strength [DNA]real.

According to a fourth aspect of the invention, there is provided an apparatus for detecting fluorescence strength from a nucleic acid amplification product in each of a plurality of reaction regions given with temperature cycles in real time, wherein fluorescence strengths [DNA]n obtained from the reaction regions every temperature cycles n are normalized using the maximum value of the fluorescence strengths [DNA]n or related value [DNA]max, and a threshold cycle number Ct is calculated by setting a threshold Th in an exponential amplification region of an amplification curve drawn using a normalized fluorescence strength [DNA]nN.

According to a fifth aspect of the invention, the fluorescence strength [DNA]nN is calculated by dividing the fluorescence strength [DNA]n for each reaction region by a value obtained by adding a value common to the reaction regions to be compared to the maximum value or related value [DNA]max.

According to a sixth aspect of the invention, the amplification curve is drawn after fluorescence strength [DNA] base before the exponential amplification region is subtracted from the fluorescence strength [DNA]n for each reaction region and the maximum value or related value [DNA]max.

According to the first aspect of the invention, in the apparatus for detecting fluorescence strength from a nucleic acid amplification product in each of a plurality of reaction regions given with temperature cycles in real time, since a fluorescence measurement value [DNA]raw obtained from the reaction region and a fluorescence measurement value [DNA]bg obtained from regions other than the reaction region adjacent to the reaction region are detected, and the fluorescence measurement value [DNA]bg is subtracted from the fluorescence measurement value [DNA]raw to determine fluorescence strength [DNA]real of the reaction region, it is possible to obtain the original fluorescence strength [DNA]real of the DNA product of the reaction region except for the fluorescence measurement value of a background by errors or contamination of the reaction region and its circumferences and way-out light for each reaction region. Accordingly, it is possible to realize preparation and quantitativeness of a correct amplification curve. In this case, with no need to use the second fluorescence signal in the prior art, it is possible to reduce time taken to acquire and process data without increase of costs and deterioration of workability.

According to the second aspect of the invention, in addition to the first aspect, since the fluorescence measurement value [DNA]bg is a simple average value of fluorescence measurement values obtained from the regions other than the plurality of reaction regions adjacent to the reaction region, or an average value of fluorescence measurement values after the fluorescence measurement values are weighted, it is possible to calculate more correct fluorescence strength of the background to determine the fluorescence strength [DNA]real with higher precision.

According to the third aspect of the invention, in addition to the first aspect or the second aspect, since the fluorescence measurement value [DNA]bg is detected every detection of the fluorescence measurement value [DNA]raw, and the fluorescence measurement value [DNA]bg is subtracted from the fluorescence measurement value [DNA]raw to determine the fluorescence strength [DNA]real, although the fluorescence strength of the background is varied during reaction, it is possible to always obtain the original fluorescence strength [DNA]real of the DNA product in real time with high precision.

According to the fourth aspect of the invention, in the apparatus for detecting fluorescence strength from a nucleic acid amplification product in each of a plurality of reaction regions given with temperature cycles in real time, since fluorescence strengths [DNA]n obtained from the reaction regions every temperature cycles n are normalized using the maximum value of the fluorescence strengths [DNA]n or related value [DNA]max, and a threshold cycle number Ct is calculated by setting a threshold Th in an exponential amplification region of an amplification curve drawn using a normalized fluorescence strength [DNA]nN, it is possible to correct and reduce unbalance of the fluorescence strength of each reaction region due to the apparatus error factors such as optical system errors, correction solution concentration errors, correction solution divisional pour errors, reaction solution divisional pour errors, etc., thereby enabling calculation of threshold cycle numbers Ct with high reliability.

According to the fifth aspect of the invention, in addition to the fourth aspect, since the fluorescence strength [DNA] nN is calculated by dividing the fluorescence strength [DNA]n for each reaction region by a value obtained by adding a value common to the reaction regions to be compared to the maximum value or related value [DNA] max, behavior of data occurring due to factors other than the apparatus error factors can be easily grasped by approximating amplification curves from the middle stage and the late stage of the cycle to actual data while suppressing the normalization effect and sufficiently securing the correction effect at the threshold.

According to the sixth aspect of the invention, in addition to the fourth aspect or the fifth aspect, since the amplification curve is drawn after fluorescence strength [DNA]base before the exponential amplification region is subtracted from the fluorescence strength [DNA]n for each reaction region and the maximum value or related value [DNA]max, it is possible to grasp the situation of the fluorescence strength from the PCR product itself, excluding the fluorescence strength generated from the reaction solution itself in the reaction region.

FIG. is a view showing another fluorescence strength state after reaction.

Figure 7:
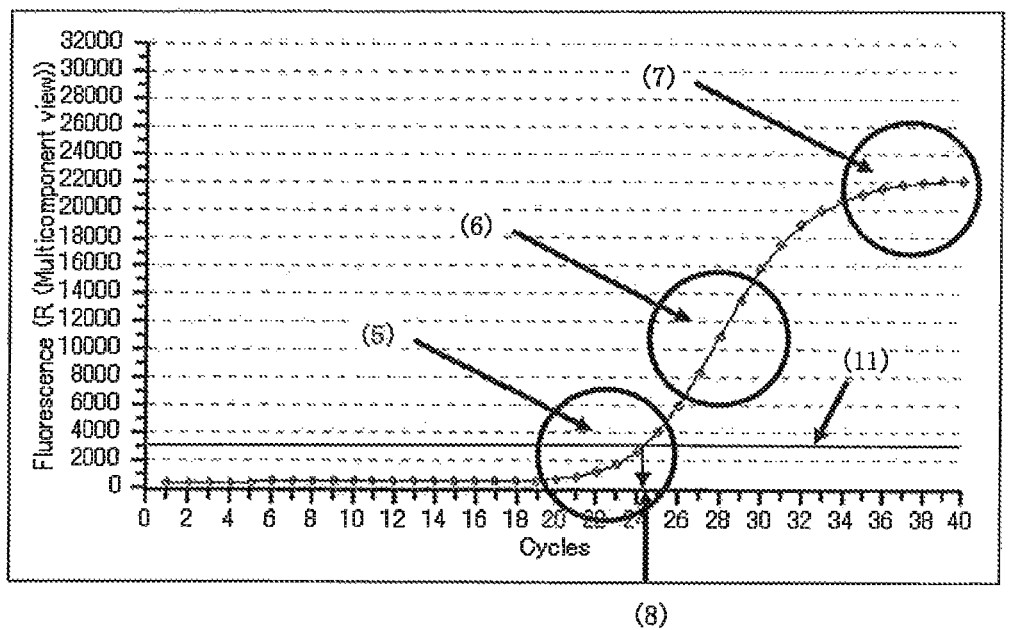

FIG. 7 shows a DNA amplification curve of a well.

Figure 8:
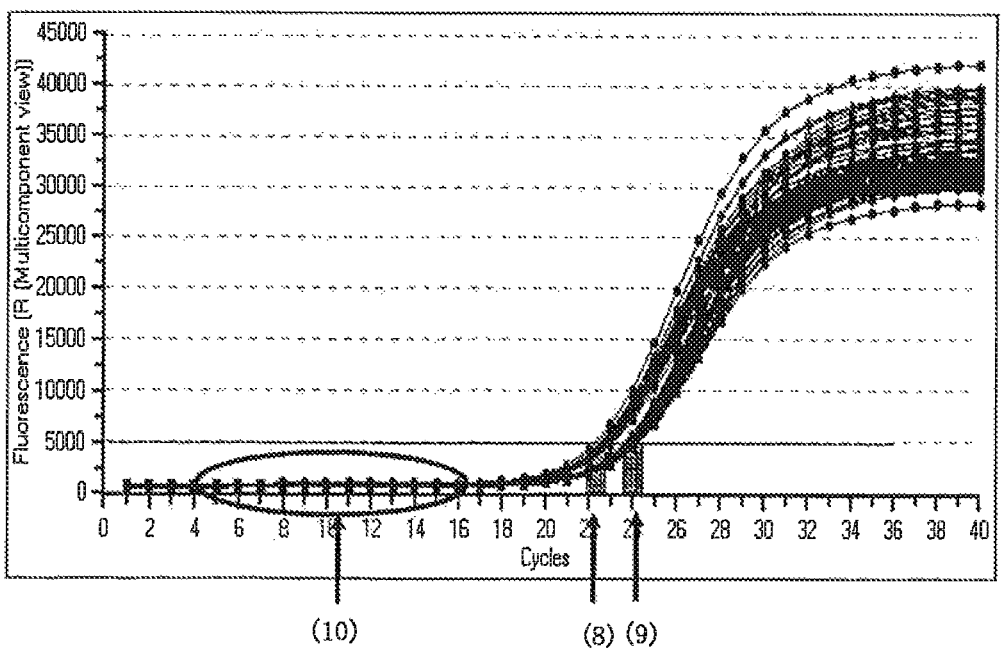

FIG. 8 shows DNA amplification curves of all wells.

Figure 9:
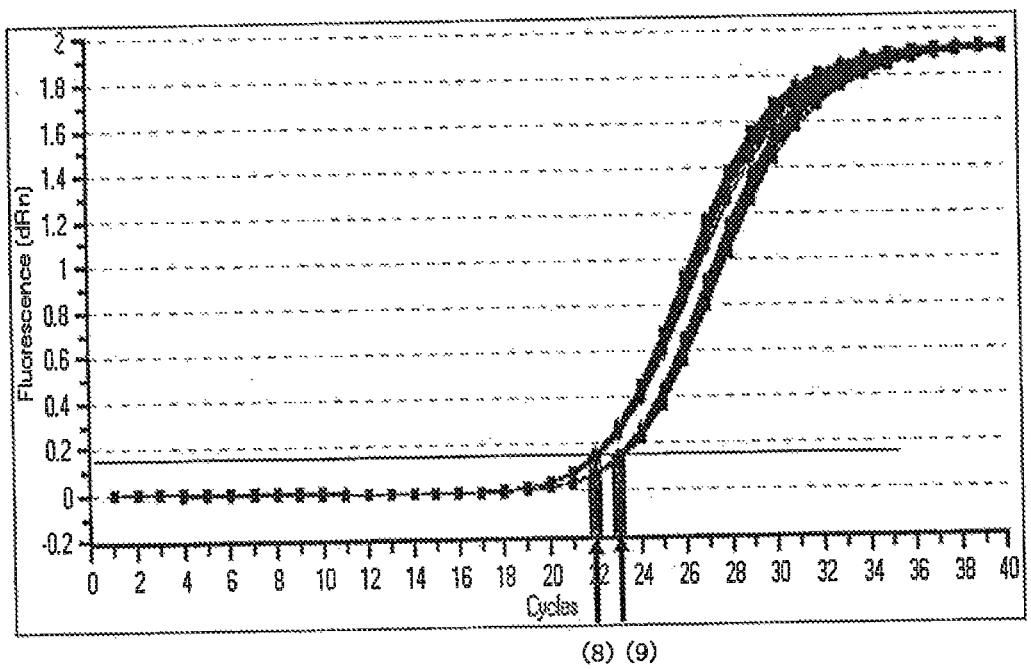

FIG. 9 shows a DNA amplification curve when the data of FIG. 8 are normalized.

Figure 10:
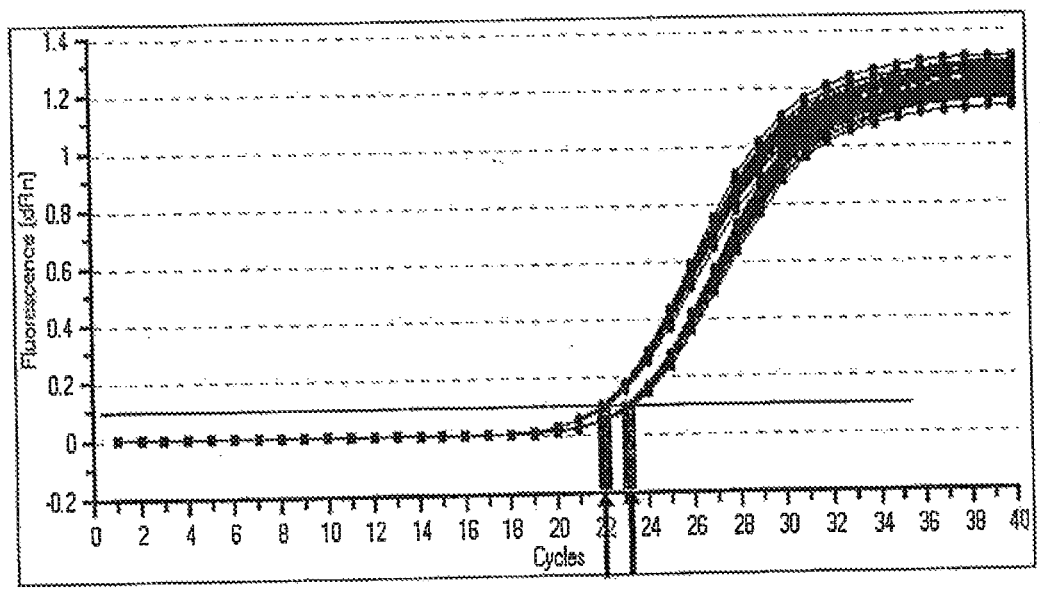

FIG. 10 shows a DNA amplification curve when the data of FIG. 8 are incompletely normalized.

Figure 1:
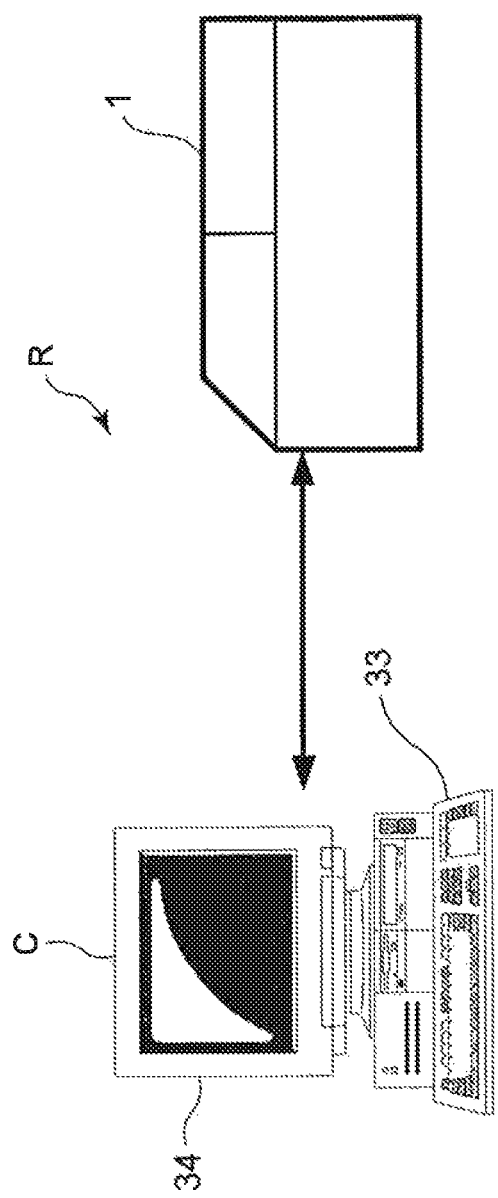
FIG. 1 is a configurational view of a real time detecting apparatus according to an embodiment of the invention.
Figure 11:
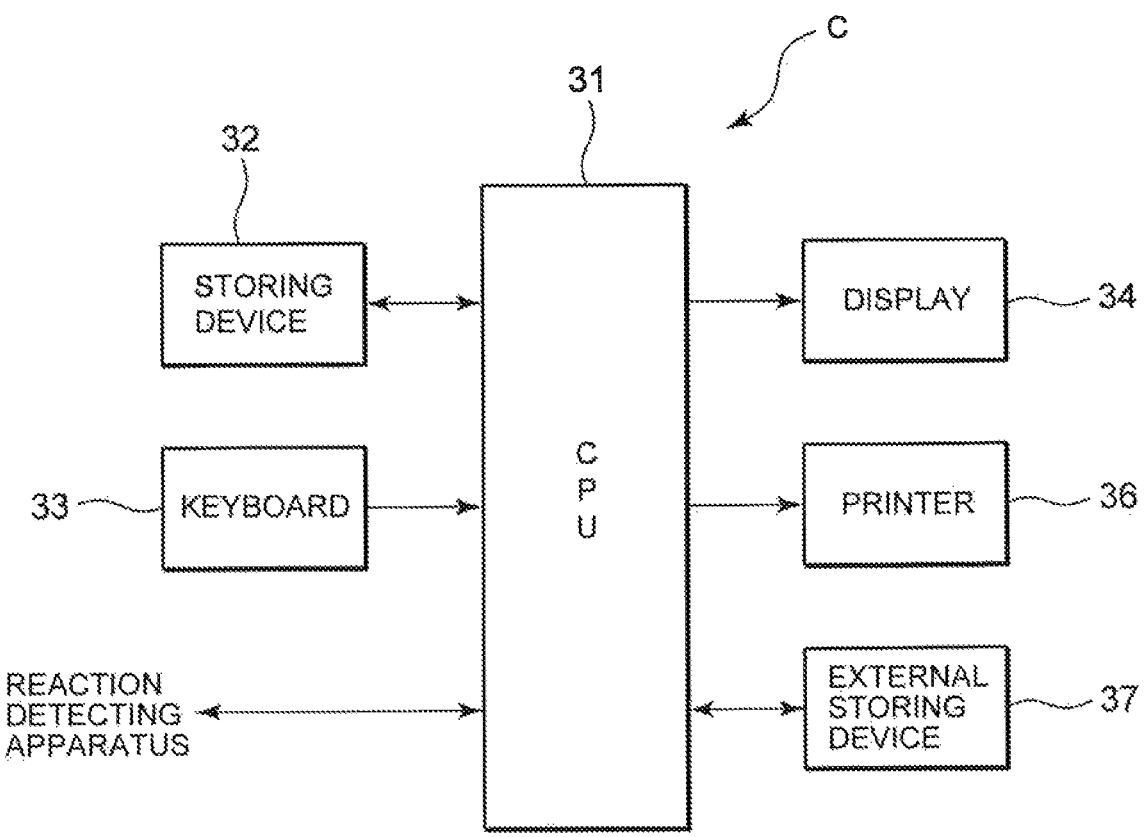

FIG. 11 is a functional block diagram of a processing apparatus constituting the real time detecting apparatus shown in FIG. 1.

DESCRIPTION OF THE PREFERRED EMBODIMENTS

Hereinafter embodiments of the present invention will be described in detail with reference to the drawings.

Embodiment 1

Figure 2:
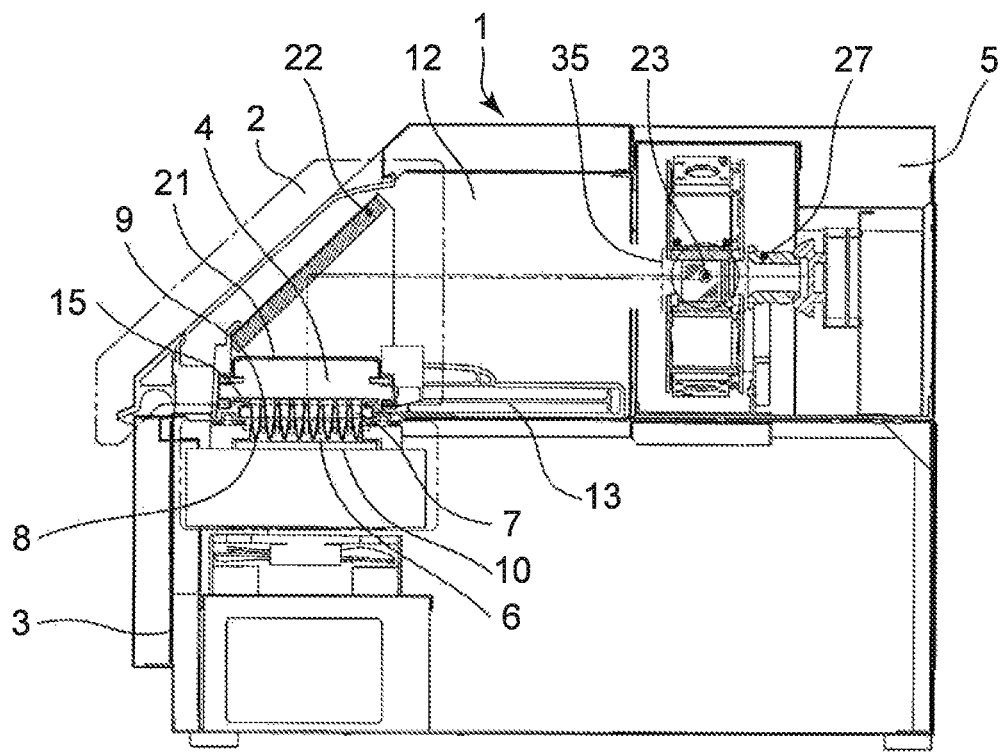
FIG. 2 is an end side view of a reaction detecting apparatus constituting the real time detecting apparatus shown in FIG. 1.
Figure 3:
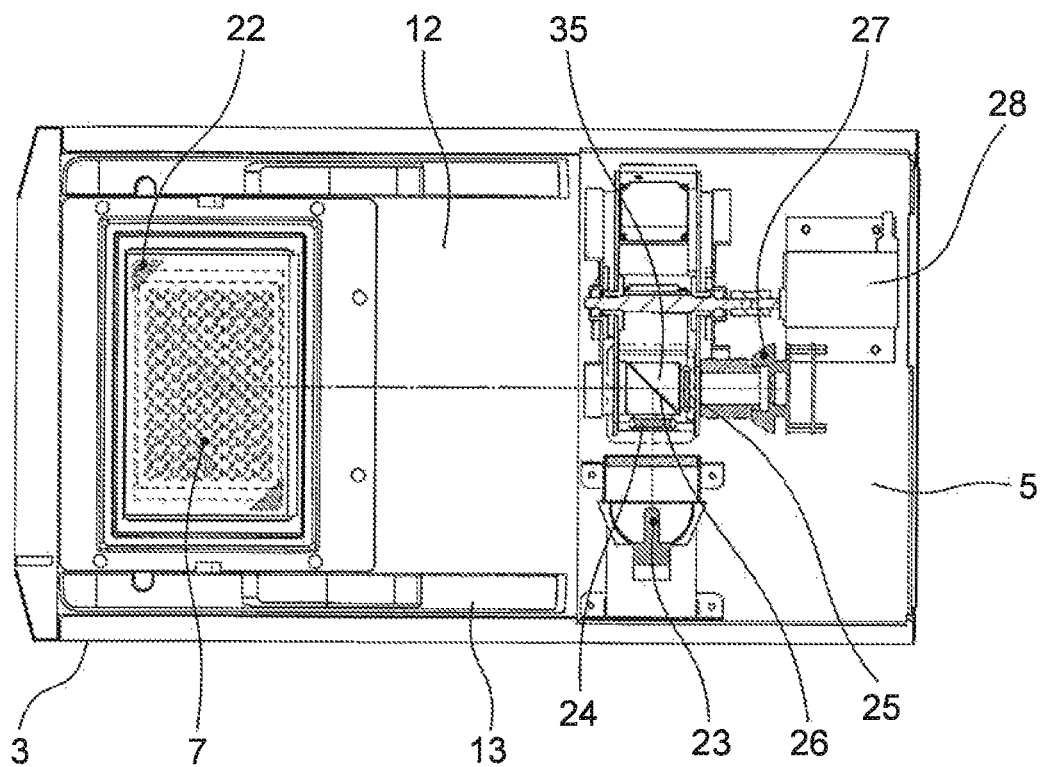
FIG. 3 is a plan sectional view of the reaction detecting apparatus shown in FIG. 2.

FIG. 1 is a configurational view of a real time detecting apparatus R according to an embodiment of the invention, FIG. 2 is an end side view of a reaction detecting apparatus 1 constituting the real time detecting apparatus R shown in FIG. 1, and FIG. 3 is a plan sectional view of the reaction detecting apparatus 1 shown in FIG. 2. The real time detecting apparatus R of the invention includes the reaction detecting apparatus 1 and a processing apparatus C such as a computer for processing detected data from the reaction detecting apparatus 1 in real time.

In this embodiment, the reaction detecting apparatus 1 is an apparatus for proliferating chromosome DNA as reaction samples and detecting a reaction state related to the proliferation by means of an optical measurement method. The reaction detecting apparatus 1 includes a body 3 having a reaction chamber 4 formed thereon, and a reaction detecting part 5 that is disposed on the body 3 in the rear of the reaction chamber 4. Within the reaction chamber 4 is provided a reaction block 6 made of thermal conductive material such as aluminum. The reaction block 6 is provided with a plurality of support holes 8 for supporting a reaction vessel 7 having a plurality of wells 7A . . . receiving a reactive solution including DNA (target template: λDNA, etc), reagent, a medium solution, etc.

The reaction vessel 7 used in this embodiment is a micro plate in which the wells 7A . . . as 96 (12×8) reaction regions are integrally formed and are connected to respective connection wells (regions other than the wells 7A (reaction regions)). The reaction vessel is not limited to a vessel having the integrally formed wells but may be a vessel having a plurality line of tubes. The number of wells 7A is not limited to this but may be, for example, 384 for ease handling. The wells 7A of the reaction vessel 7 have its opened top side attached with a seal cap 9 for preventing a reaction solution from being evaporated due to temperature treatment of the reaction solution. In this embodiment, light transmissive synthetic resin material is used for detection of fluorescence strength since the detection can be achieved when light passes through the cap 9.

Within the body 2 is provided a peltier device 10 for heating and cooling the reaction block 6. The peltier device 10 is temperature-controlled by a controller (not shown) and heats and cools the reaction block 6 cyclically, thereby cultivating (amplifying) DNA (reaction samples) within the wells 7A of the reaction vessel 7.

In this embodiment, a dark chamber component part 12 is provided in the other end from the reaction detecting part 5 provided on the rear top side of the body 2, that is, over the front top side of the body 2 in which the reaction chamber 4 is formed. The front side of the dark chamber component part 12 is forward opened, and the cover 2 inclined low toward the front is provided in this forward opening in a freely opened/closed manner. The cover 2 is moveable backward and forward by a rail member 13 formed from the front side of the dark chamber component part 12, that is, the top front side of the body 3 to an inner rear side of the dark chamber component part 12. In a state where the cover 2 is moved backward, the cover 2 is received in the dark chamber component part 12.

Within the cover 2, a pressing member 15 for pressing the reaction vessel 7 against the reaction block 6 of the reaction chamber 4 is movably provided to face the reaction block 6, with the cover 2 blocked. The pressing member 15 is a plate made of aluminum having good thermal conductivity and is provided with a plurality of transparent holes in correspondence to the top of the wells 7A.

On the top side of the pressing member 15 is disposed a Fresnel screen 21 as an optical lens. The Fresnel screen 21 generally has a plurality of grooves which are formed on its plane and reflect and extend incident light. At this time, the Fresnel screen 21 has an optical property to collimate the incident light to be completely or nearly parallelized when the incident light is reflected and extended, thereby allowing the incident light to be transmitted along its optical path corrected for distortion.

In the meantime, a reflecting plate 22 is disposed on a surface constituting the reaction chamber 4 side of the cover 2 blocking the front top side of the reaction chamber 4 in the top of the reaction block 6. In this embodiment, the reflecting plate 22 is formed of a flat mirror or the like and serves to reflect light from a light source lamp 23, which will be described in detail later, toward the Fresnel screen 21.

In the meantime, the reaction detecting part 5 contains the light source lamp 23, a filter unit 35 having a plurality of band pass filters, a reflecting plate 26, a CCD camera 27 and a filter driver 28 for rotating the filter unit 35.

The light source lamp 23 is a lamp for emitting light including excitation light for exciting fluorescence from a reaction solution depending on the amount of a DNA product to be detected in the reaction solution. A halogen lamp is typically used as the light source lamp 23. The reflecting plate 26 reflects light having a predetermined wavelength, which is emitted from the light source lamp 23, at a predetermined angle, and polarizes the reflected light t the reflecting plate 22. The reflecting plate 26 has a property to transmit predetermined fluorescence. In this embodiment, when the light from the light source lamp 23 disposed in the side of the reaction detecting part 5 is forward reflected by the reflecting plate 26, the reflecting plate 22 is irradiated with the light from the light source lamp 23.

The filter unit 35 is a unit configured by arranging various kinds of band pass filters in the form of a wheel. This filter unit 35 is rotated by the filter driver 28. The band pass filters are selected and positioned between the light source lamp 23 and the reflecting plate 26 or between the reflecting plate 22 and the camera 27. In the figure, a band pass filter 24 is positioned between the light source lamp 23 and the reflecting plate 26 and a band pass filter 25 is positioned between the reflecting plate 22 and the camera 27.

The band pass filter 24 is an optical filer having a property to pass only light having a wavelength, which is required to excite fluorescence from the reaction solution, of components of the light from the light source lamp 23. The light passed the filter 24 becomes excitation light for exciting the fluorescence from a specified component of the reaction solution.

The band pass filter 25 is an optical filter having a property to pass fluorescence generated from the reaction solution in the wells 7A of the reaction vessel 7 and a predetermined fluorescence component from reflected light through the reflecting plate 22. Here, reflected light components other than the predetermined fluorescence component are intercepted.

The camera 27 is a device for detecting the fluorescence passed the band pass filter 25. A fluorescence image detected by the camera 27 is inputted to the controller and is sent to the processing apparatus C for analysis of concentration, i.e., amount of amplification, of the reaction solution. In addition, these band pass filers 24 and 25 may be selectively used in any combination thereof based on the reaction solution to be detected and the kind of fluorescence pigment used corresponding to the reaction solution.

With the above configuration, the controller controls the peltier device 10 to set the reaction solution in the reaction vessel 7 supported by the support holes 8 of the reaction block 6 to be, for example, a thermal deformation temperature of +95° C., and then performs a thermal deformation process to thermally deform the reaction solution. Subsequently, the controller controls the peltier device 10 to cool the reaction block 6 to, for example, +60° C., and then performs an annealing process and an expansion process for DNA in the thermally-deformed reaction solution that is received in the reaction vessel 7. The controller performs cultivation (amplification) of DNA and the like according a PCR method by repeating one cycle including the thermal deformation process, the annealing process and the expansion process several times, for example, 40 times.

During or after this cultivation, the reaction detecting part 5 performs a detection operation regularly, such as after one cycle, in order to detect an amplification state of DNA of the reaction solution in the reaction vessel 7. In the detection operation, first, light emitted from the light source lamp 23 reaches the reflecting plate 26 through the band pass filter 24. The band pass filter 24 passes only light having a wavelength required to excite fluorescence, that is, excitation light, of the light from the light source lamp 23. The reflecting plate 26 reflects the excitation light toward the reflecting plate 22 through the dark chamber component part 12. The reflecting plate 22 again reflects the excitation light toward the Fresnel screen 21 provided in the reaction block 6, that is, from the top to the bottom.

The excitation light impacting on the Fresnel screen 21 is condensed by the lens 21 and is changed in its incident angle to an angle which is parallel or nearly parallel to the wells 7A of the reaction vessel 7 received in the reaction block 6. Accordingly, the excitation light passed the lens 21 is incident into the wells 7A with an incident angle which is parallel or nearly parallel through the transparent holes formed in the pressing member 15.

When the DNA in the well 7A beforehand added with predetermined fluorescence pigment is irradiated with the excitation light incident at the parallel or nearly parallel angle in the wells 7A, fluorescence is generated depending on the amount of PCR product. The generated fluorescence and other reflected light from the PCR product reach the reflecting plate 22 through the transparent holes formed in the pressing member 15 formed in the pressing member 15 and the Fresnel screen 21 as well.

Thereafter, the fluorescence and the other reflected light that reached the reflecting plate 22 form an optical path in a substantial horizontal direction within the dark chamber component part 12 by the action of the reflecting plate 22 and reaches the camera 27 through the band pass filter 25 facing the reflecting plate 22. In this case, since the cover 2 is blocked within the dark chamber component part 12, a dark chamber is formed, thereby avoiding attenuation of fluorescence.

At this time, since the reflecting plate 26 is made of fluorescence transmissive material, the reflected light and the fluorescence that passes the reflecting plate 26 reaches the band pass filter 25. Only specified fluorescence can be passed through the band pass filter 25 depending on the kind of the filter 25, as described above, only the specified fluorescence can reach the camera 27 disposed in the rear of the filter 25.

When the camera 27 take an image of the received fluorescence, a fluorescence state of the PCR products in the wells 7A of the reaction vessel 7 is detected. Detection data (image data shown in FIGS. 4 to 6) on the detected fluorescence state of the PCR products are sent from the controller to the processing apparatus C. The processing apparatus C analyzes the detection data to detect the concentration of the samples, that is, the amount of amplification of DNA and the like. Since the positional relation between the positions of the wells 7A and the image is known in advance, by obtaining the brightness of pixels of the image of the wells 7A, fluorescence strength of the wells 7A can be measured and the amount of PCR products can be detected from the measured fluorescence strength.

The processing apparatus C includes an arithmetic processing part (CPU) 31 for performing the detection data sent from the reaction detecting apparatus 1, a storage device (storing means) 32 connected to the arithmetic processing part 31, a keyboard (or input means such as a mouse) 33, a display (output means) 34, a printer (output means) 36, an external storing device 37 such as FD, CD, DVD, memory or the like, etc., as shown in FIG. 11. The detection data sent from the reaction detection apparatus 1 is stored in the storing device. 32 and is displayed on the display 34 and so on after being subjected to the following process by the arithmetic processing part 31.

Figure 5:
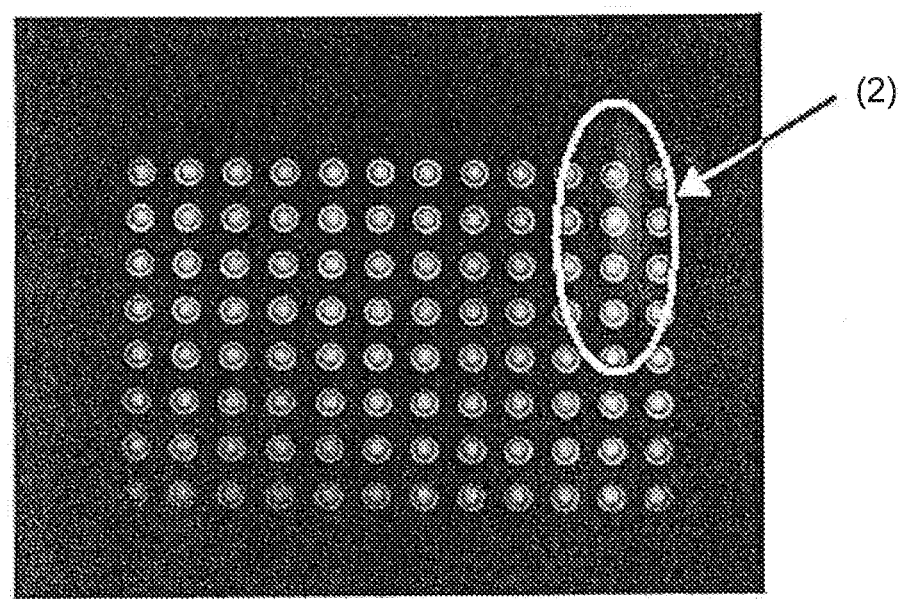
FIG. 5 is a view showing a fluorescence strength state after reaction.
Figure 6:
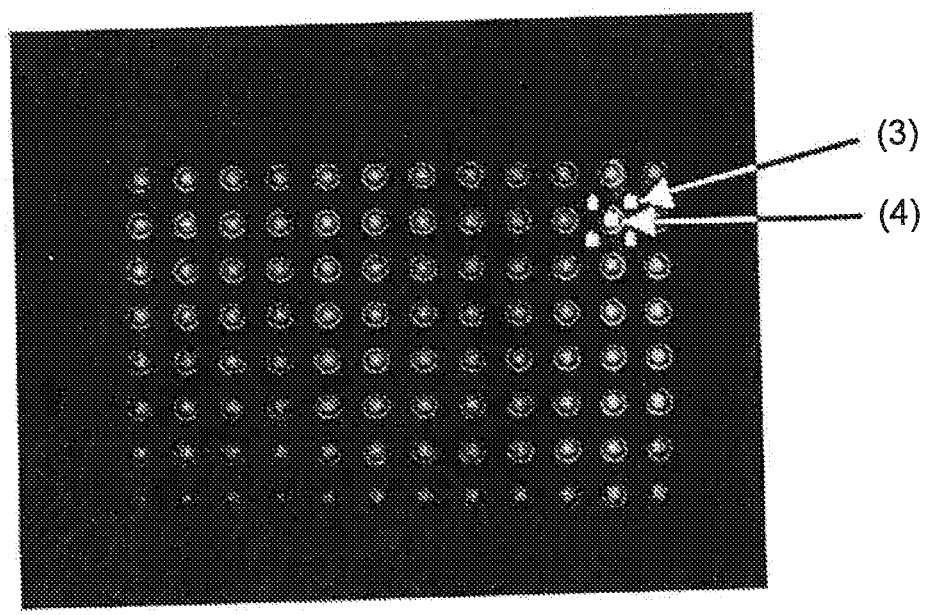

Next, a process sequence of the detection data in the processing apparatus C will be described. FIGS. 5 and 6 show images of the detection data sent from the reaction detecting apparatus 1 to the processing apparatus C. 96 annular images appearing to be white are fluorescence generated from the PCR products in the wells 7A. In this embodiment, with SYBR PREMIX EX TAQ (registered trademark) as a base, a reaction solution is adjusted from PCR Forward Primer, PCR reverse Primer, Template (λDNA given as an initial value) and dH$_2$O. In FIGS. 5 and 6, a reaction solution having the concentration of 0.2 pg/μL is divisionally poured in 48 upper half wells 7A (X group) and a reaction solution having the concentration of 0.4 pg/μL is divisionally poured in 48 lower half wells 7A (Y group). The temperature cycle number is 40.

When the temperature cycle number progresses from reaction initiation, the fluorescence strength increases according to the amount of amplification of DNA. Plotting this procedure is the amplification curve of FIG. 7 as described above. This amplification curve is obtained for each well 7A and is displayed on the display 34 (FIG. 8). When the keyboard (or mouse) 33 is used to set a threshold Th ((11) in FIG. 7) in an exponential amplification region ((5) in FIG. 7), cycle number Ct at that point (threshold cycle number Ct) is read to 24.5 in this figure. Since there is a correlation between the threshold cycle number Ct and the initial amount of DNA of a test sample, a calibration curve representing this linear relation can be prepared. The arithmetic processing part 31 estimates the initial amount of DNA of the test sample based on this calibration. This enables correct quantitativeness based on a PCR amplification speed theory.

(A) Removal of Apparatus Error Factors

Figure 4:
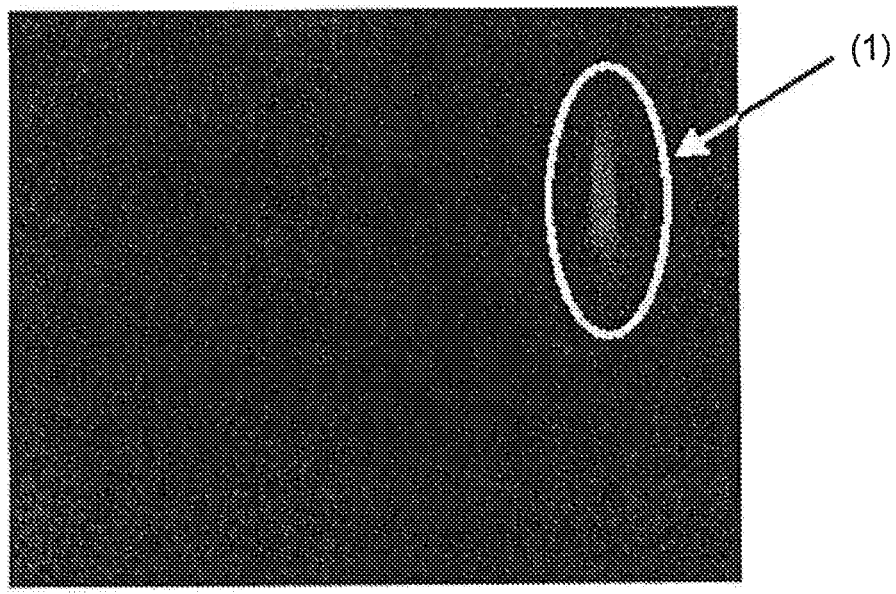
FIG. 4 is a view showing a fluorescence strength state of a background of a reaction vessel.

As described above, before the reaction initiation, the brightness of pixels in the image data obtained by the camera 27 of the reaction detecting apparatus 1 is not necessarily constant and there occurs a spot due to contamination of the optical system or way-out light as indicated by (1) in FIG. 4. When the PCR reaction is progressed, this spot overlaps with the images of the wells 7A as shown in FIG. 5, wastefully adding to the fluorescence strength of the wells 7A.

So, the arithmetic processing part 31 of the processing apparatus C performs the following process in order to obtain the original fluorescence strength of the wells. That is, for example, in case of a well 7A lying in a stage (B11) second from the right side and second from the top side in FIG. 6, a fluorescence measurement value [DNA]rawB11 of the well 7A ((4) in FIG. 6) of the B11 stage is measured and stored in the storing device 32. Next, 4 adjacent fluorescence measurement values [DNA]bg1, [DNA]bg2, [DNA]bg3 and [DNA]bg4 in a connection wall portion near the well 7A of the B11 stage are measured and an average value of the 4 fluorescence measurement values (a fluorescence measurement value of a background) is obtained and stored in the storing device 32. Then, according to the following Equation (2), by subtracting the average value from the fluorescence measurement value [DNA]rawB11, the original fluorescence strength [DNA]realB1 of the well 7A of the B11 stage is calculated.

$$[DNA]realB11 = [DNA]rawB11 - (([DNA]bg1 + [DNA]bg2 + [DNA]bg3[DNA]bg4)/4) \quad (2)$$

This process is performed for all 96 wells every detection of the fluorescence measurement value [DNA]raw to determine the original fluorescence strength [DNA]real of all wells 7A. Thus, it is possible to obtain the original fluorescence strength [DNA]real of the DNA product of the well 7A except for the fluorescence measurement value [DNA]bg of the background by errors or contamination of the well 7A and its circumferences and way-out light for each well 7A (reaction region).

Accordingly, it is possible to realize preparation and quantitativeness of a correct amplification curve. In this case, with no need to use the second fluorescence signal in the prior art, since an arithmetic process may have only to be performed in the processing apparatus C, it is possible to reduce time taken to acquire and process data without increase of costs and deterioration of workability.

In this embodiment, although the 4 adjacent fluorescence measurement values [DNA]bg1, [DNA]bg2, [DNA]bg3 and [DNA]bg4 near the well 7A are measured and their average value is subtracted from the fluorescence measurement value [DNA]raw, the present invention is not limited to this but the average value may be one point value or an average value of two or three points. However, when the 4 point average value is used as in this embodiment, it is possible to calculate more correct fluorescence strength of the background to determine the fluorescence strength [DNA]real with higher precision. In addition, although a simple average of the 4 point fluorescence measurement values near the well 7A is used in this embodiment, the present invention is not limited to this, but points may be weighted and averaged in consideration of spots of contamination conditions.

Variation (drift) of the fluorescence strength of the background before and after reaction is not clear. However, in this embodiment, since the fluorescence measurement values [DNA]bg1 to [DNA]bg4 are detected every detection of the fluorescence measurement value [DNA]raw and the average value of the fluorescence measurement values [DNA]bg1 to [DNA]bg4 is subtracted from the fluorescence measurement value [DNA]raw to determine the fluorescence strength [DNA]real, although the fluorescence strength of the background is varied during reaction, it is possible to always obtain the original fluorescence strength [DNA]real of the DNA product in real time with high precision.

(B) Normalization 1

Next, FIG. 8 shows DNA amplification curves of all 96 wells 7A. In the figure, a horizontal axis represents temperature cycle number and a vertical axis represents fluorescence strength. As described above, since the reaction solutions having different concentrations divided into the upper half X group and the lower half Y group in FIGS. 5 and 6 are divisionally poured, a reaction curve have to appear as two lines originally. In addition, the threshold cycle number Ct will also be two. However, due to apparatus error factors such as the above-mentioned optical system errors, correction solution concentration errors, correction solution divisional pour errors, reaction solution divisional pour errors, etc., the amplification curve of each well 7A may be unbalanced and a plurality of threshold cycle numbers Ct may occurs as indicated by (8) and (9) in FIG. 8 (unbalance).

So, the arithmetic processing part 31 normalizes data based on a predetermined selection command from the keyboard (or mouse) 33. That is, the arithmetic processing part 31 obtains fluorescence strength [DNA]nN normalized by the following Equation (3) using the fluorescence strength [DNA]n (the original fluorescence strength [DNA]real at an n-th temperature cycle number) determined every temperature cycle numbers n and stored in the storing device 32, the fluorescence strength maximum value [DNA]max (the maximum of fluorescence strengths [DNA]real up to the temperature cycle numbers n, this is stored in the storing device 32) for each well 7A, and a value Z common to wells 7A (all wells 7A in this embodiment) to be compared.

$$[DNA]nN=[DNA]n/([DNA]max+Z) \quad (3)$$

By this process, the fluorescence strength of each well 7A is normalized. FIG. 9 shows a case of Z=0. Since unbalance of the fluorescence strength due to the apparatus error factors of each well 7A is corrected and reduced by this normalization, unbalance of the threshold cycle numbers Ct in the X group and the Y group can be further reduced as compared to FIG. 8. This enables calculation of threshold cycle numbers with high reliability. In addition, FIG. 9 shows multiplication of [DNA]nN by a value common to all wells in order to set the whole scale to be a proper value.

(C) Normalization 2

Here, the fluorescence strength in a plateau region in the late of cycle may be unbalanced due to unbalance of chemical reaction in addition to the above-mentioned apparatus error factors. It is believed that such a chemical reaction factor has no proportional effect on the fluorescence strength in an exponential amplification region. That is, in some cases, fluorescence strengths in regions having the plateau effect had better not to be completely matched each other.

In this case, the keyboard (or mouse) 33 is used to increase the Z value of the above Equation (3). FIG. 10 shows amplification curves for wells 7A in case of Z=20000. Increase of the Z value means weakening of the normalization effect. However, it can be seen from FIG. 10 that behavior of the amplification curves from the middle stage to the late state of the cycle approximates to behavior of actual fluorescence strength (see FIG. 8). In the meantime, it can be seen from this figure that the correction effect at the threshold is sufficiently secured. Accordingly, by approximating the amplification curves from the middle stage and the late stage of the cycle to actual data while suppressing the normalization effect and sufficiently securing the correction effect at the threshold, behavior of data occurring due to factors other than the apparatus error factors can be easily grasped.

Here, when such incomplete normalization is made, the Z value may be determined according to the following Equation (4).

$$Z=\alpha[DNA]max+\beta \quad (4)$$

Where, $\alpha$ and $\beta$ are coefficients common to the wells 7A.

In addition, the arithmetic processing part 31 calculates the above-described maximum value [DNA]max as a moving average of fluorescence strengths. This is because the fluorescence strength [DNA]real shows a saw shape actually. However, the maximum value used for the normalization may be a peak value of the saw shape or, for example, 90% of the peak value (either being related to the maximum value).

(D) Correction of Baseline

Here, although (10) in FIG. 8 is a region of a level at which a reaction result can not be detected at the initial stage of cycle, since the reaction solution itself in the wells 7A initially generates predetermined fluorescence, the fluorescence strength is not generally zero in this region. So, the arithmetic processing part 31 corrects a baseline based on an instruction from the keyboard (or mouse) 33. That is, the arithmetic processing part 31 sets an average value [DNA] base of the fluorescence strengths of the well 7A in the region 10 at the initial stage of cycle to be a baseline and performs the above-described normalization process after subtracting the average value from the above-mentioned [DNA]n and [DNA]max. The reason for this process is that the initial fluorescence strength is set to be zero in FIGS. 9 and 10 [DNA]base may use the minimum value of [DNA]n).

Accordingly, it is possible to grasp the situation of the fluorescence strength from the PCR product itself, excluding the fluorescence strength generated from the reaction solution itself in the wells 7A.

It should be understood that material, amount and number shown in this embodiment are not particularly limited.

What is claimed is:

1. A method for detecting fluorescence strength from a nucleic acid amplification product in real time in each of a plurality of reaction regions in a reaction vessel undergoing temperature cycling, comprising the steps of:
    subjecting a reaction vessel having a plurality of reaction regions oriented in a rectangular array, to temperature cycling;
    after a temperature cycle, detecting, using an optical system fluorescence measurement, separately for each of the reaction regions in the reaction vessel:
    a value [DNA]raw from the reaction region; and
    a fluorescence measurement value [DNA]bg, obtained from four separate regions, each of which is outside the reaction region and in a connection wall portion adjacent to the reaction region; and
    subtracting the fluorescence measurement value [DNA]bg from the fluorescence measurement value [DNA]raw every time the fluorescence measurement value [DNA] raw is detected for each of the reaction regions separately to determine fluorescence strength [DNA]real of each of the reaction regions.

2. The method according to claim 1, wherein the detecting and subtracting steps are performed after each temperature cycle.

3. The method according to claim 1, wherein, in the detecting step, for each reaction region, the fluorescence measurement value [DNA]bg for the reaction region is a simple average value or a weighted average value of the four fluorescence measurement values from the four separate regions for that reaction region.

* * * * *